US011778288B2

(12) United States Patent
Harter et al.

(10) Patent No.: US 11,778,288 B2
(45) Date of Patent: Oct. 3, 2023

(54) SENSOR ARRAY, METHOD FOR CALCULATING A COLOR IMAGE AND A HYPERSPECTRAL IMAGE, METHOD FOR CARRYING OUT A WHITE BALANCE AND USE OF THE SENSOR ARRAY IN MEDICAL IMAGING

(71) Applicant: Scholly Fiberoptic GmbH, Denzlingen (DE)

(72) Inventors: Daniel Harter, Emmendingen (DE); Johannes Bourbon, Freiburg (DE)

(73) Assignee: Scholly Fiberoptic GmbH, Denzlingen (DE)

(*) Notice: Subject to any disclaimer, the term of this patent is extended or adjusted under 35 U.S.C. 154(b) by 447 days.

(21) Appl. No.: 17/002,864

(22) Filed: Aug. 26, 2020

(65) Prior Publication Data
US 2021/0067712 A1 Mar. 4, 2021

(30) Foreign Application Priority Data

Aug. 30, 2019 (DE) .......................... 102019123356.9

(51) Int. Cl.
*H04N 5/33* (2023.01)
*H01L 27/146* (2006.01)
(Continued)

(52) U.S. Cl.
CPC ......... *H04N 23/11* (2023.01); *A61B 1/00009* (2013.01); *A61B 1/044* (2022.02);
(Continued)

(58) Field of Classification Search
CPC .. H04N 5/332; H04N 9/0451; H04N 9/04553; H04N 9/04559; H04N 9/735;
(Continued)

(56) References Cited

U.S. PATENT DOCUMENTS 9,013,623 B2    4/2015 Schmid et al.
2011/0228097 A1* 9/2011 Motta .................. H04N 25/131
                                                348/E5.09

FOREIGN PATENT DOCUMENTS

DE    102010030108    12/2011
DE    102016122790    6/2017
(Continued)

OTHER PUBLICATIONS

Shrestha, Raja et al., "CFA Based Simultaneous Multispectral Imaging and Illuminant Estimation", in: Computational Color Imaging, CCIW 2013, LNCS 7786, pp. 158-170, 2013.
(Continued)

*Primary Examiner* — Howard D Brown, Jr.
*Assistant Examiner* — Tyler B Edwards
(74) *Attorney, Agent, or Firm* — Volpe Koenig

(57) ABSTRACT

A sensor array (1) for recording a color image in the visible spectrum (8) and hyperspectral information that is spatially linked with the color image, wherein the sensor array (1) includes an image sensor (2) composed of a plurality of photocells (3), wherein respectively a color filter (4) is fixedly assigned to at least one portion of the photocells (3), wherein each photocell (3) is assigned to a subcell (5) and each subcell (5) is assigned to a supercell (6). Each subcell (5) has at least one additional filter of a channel, and all the channels together cover at least the entire visible spectrum
(Continued)

(8), and the characteristic wavelengths (9) of the individual filters belonging to a channel in each case differ from one another between the subcells (5) of a supercell (6).

21 Claims, 4 Drawing Sheets

(51) Int. Cl.
| | |
|---|---|
| H04N 9/04 | (2006.01) |
| H04N 9/73 | (2023.01) |
| G01J 3/28 | (2006.01) |
| A61B 5/00 | (2006.01) |
| A61B 1/00 | (2006.01) |
| H04N 23/11 | (2023.01) |
| G01J 3/51 | (2006.01) |
| A61B 1/04 | (2006.01) |
| H04N 23/84 | (2023.01) |
| H04N 23/88 | (2023.01) |
| H04N 25/131 | (2023.01) |
| H04N 25/13 | (2023.01) |

(52) U.S. Cl.
CPC .......... *A61B 5/0035* (2013.01); *A61B 5/0075* (2013.01); *G01J 3/2803* (2013.01); *G01J 3/2823* (2013.01); *G01J 3/513* (2013.01); *H01L 27/14621* (2013.01); *H01L 27/14645* (2013.01); *H04N 23/84* (2023.01); *H04N 23/88* (2023.01); *H04N 25/131* (2023.01); *H04N 25/135* (2023.01); *G01J 2003/2826* (2013.01)

(58) Field of Classification Search
CPC ... A61B 1/00009; A61B 1/044; A61B 5/0035; A61B 5/0075; A61B 1/00186; A61B 1/043; A61B 1/051; G01J 3/2803; G01J 3/2823; G01J 3/513; G01J 2003/2826; G01J 2003/2806; H01L 27/14621; H01L 27/14645
See application file for complete search history.

(56) References Cited

U.S. PATENT DOCUMENTS

| | | | |
|---|---|---|---|
| 2012/0127292 A1* | 5/2012 | Yamazaki | A61B 1/0638 348/E7.085 |
| 2013/0286237 A1 | 10/2013 | Samadani et al. | |
| 2016/0088265 A1* | 3/2016 | Lu | H01L 27/14627 348/280 |
| 2017/0171523 A1* | 6/2017 | Radakovic | H04N 5/2256 |

FOREIGN PATENT DOCUMENTS

| | | |
|---|---|---|
| EP | 1196081 | 8/2013 |
| EP | 2252199 | 5/2019 |
| WO | 2015077493 | 5/2015 |
| WO | 2018073824 | 4/2018 |

OTHER PUBLICATIONS

Hardeberg, Jon Yngve et al., "Multispectral color image capture using a liquid crystal tunable filter" Opt. Eng., pp. 2532-2548, Oct. 1, 2002.

Shrestha, Raju, et al., Computational color constancy using chromagenic filters in color filter arrays, Proc. SPIE 8298, Sensors, Cameras, and Systems for Industrial Scientific Applications XIII, 82980S, Feb. 15, 2012.

* cited by examiner

SENSOR ARRAY, METHOD FOR CALCULATING A COLOR IMAGE AND A HYPERSPECTRAL IMAGE, METHOD FOR CARRYING OUT A WHITE BALANCE AND USE OF THE SENSOR ARRAY IN MEDICAL IMAGING

INCORPORATION BY REFERENCE

The following documents are incorporated herein by reference as if fully set forth: German Patent Application No. 10 2019 123 356.9, filed Aug. 30, 2019.

TECHNICAL FIELD

The invention relates to a sensor array comprising an image sensor composed of a plurality of photocells, wherein the photocells are at least partly assigned respectively a color filter. In particular, the sensor array can be configured for recording a color image in the visible spectrum and a hyperspectral image.

In addition, the invention relates to a method for calculating a color image and a hyperspectral image.

Furthermore, the invention relates to a method for carrying out a white balance for a sensor array.

Finally, the invention also relates to a use of a sensor array in medical imaging.

BACKGROUND

Sensor arrays are already known in which color filters of individual color channels (for example Red, Green and Blue (RGB) or Cyan, Magenta and Yellow (CMYK)) are combined with an in particular monochromatic image sensor. In this case, the image sensor has a multiplicity of small light-sensitive areas, so-called photocells, upstream of which in the optical beam path there is respectively arranged a color filter. The photocell can thus detect only a brightness value for light in a wavelength range which is transmitted through the upstream color filter. Sensor arrays of this type are known by the designation "Bayer sensor", for example.

SUMMARY

The invention is based on the object of extending the possibilities for application of previously known sensor arrays of the type mentioned in the introduction.

This object is achieved by a sensor array of the type mentioned in the introduction having one or more of the features described herein.

In particular, therefore, according to the invention, in order to achieve the object, a sensor array of the type mentioned in the introduction is provided which is characterized by the fact that the photocells are grouped in subcells and the subcells are grouped in supercells, that each subcell has at least one color filter of a color channel, wherein all the color channels together cover the entire visible spectrum, that the characteristic wavelengths of the color filters belonging to one color channel, in each case at least partly differ from one another between the subcells of a supercell. Provision can thus be made, for example, for all the subcells in pairs to have different characteristic wavelengths or for individual color filters to have corresponding characteristic wavelengths between two subcells. By way of example, the characteristic wavelengths can differ from subcell to subcell only with regard to one color channel or to a selection among all the color channels, or individual characteristic wavelengths can correspond within a color channel while other characteristic wavelengths in this color channel differ within the supercell. Mixed forms of these individual cases are also able to be realized.

By way of example, the subcells of a supercell can have color filters according to the pattern RGBX (R=red, G=green, B=blue, X=further spectral range, for example IR), wherein R, G and B are color filters having in each case a uniform characteristic wavelength over the subcells, while the color filter X has an individual characteristic wavelength from subcell to subcell.

One configuration of the invention provides for the characteristic wavelengths of the color filters belonging to one color channel to differ from one another in each case between the subcells of a supercell. Consequently, a different characteristic wavelength is selectable for each pixel within at least one color channel, such that redundancies are avoidable.

One configuration of the invention provides for the characteristic wavelengths of the color filters belonging to all the color channels to differ from one another in each case between the subcells of a supercell. Consequently, a different characteristic wavelength is selectable for each pixel, such that redundancies are avoidable.

Preferably, provision can be made here for each subcell to have a color filter from a specific spectral range and for all the subcells within a supercell together to cover at least the spectral range of the primary colors of the visible spectrum. With further preference, the wavelength ranges of the color filters belonging to a spectral range can differ from one another in each case between the subcells of a supercell insofar as the ranges covered by the color filters can overlap, but are not identical.

The sensor array according to the invention thus makes it possible to record both a color image of relatively high resolution in a spectrum visible to the human eye and, in addition thereto, a hyperspectral image using only one image sensor. Consequently, the color image can be able to be reconstructed from the different spectral ranges of the individual subcells, while the spectral information is obtained from the individual subcells. The term "hyperspectral image" within the meaning of the application can be understood to the effect that it should also be understood to mean a multispectral image and/or multispectral information, depending on how many different color filters are used per supercell and/or depending on the chosen magnitude of the filter widths of the filters used and/or of the distance between the filters. In other words, this can be taken to mean information in the form of a spectroscopic measurement value that is additional to the information of the color image and is spatially linked with the information of the color image. The additional information gives rise, particularly in the medical field, to a multiplicity of possibilities for offering a user of a medical imaging method, for example, support in the assessment and evaluation of the image scene represented on the image. What is thus particularly advantageous with the use of just a single image sensor having the configuration according to the invention is the possibility of being able to detect additional hyperspectral information in a recorded image scene, without an incorrect spatial assignment, e.g. on account of an erroneous orientation of two image sensors with respect to one another, being able to occur in the process. Consequently, the solution according to the invention does not require a spatial coordination (registration), as is required in previously known sensor arrays having two image sensors—one for the color image and one for the hyperspectral image. The use of just one image sensor is made possible by the provision of a structural arrangement of the individual filters in subcells and an arrangement of the subcells in supercells, wherein tuning of the individual filters of a supercell is required, such that in particular the characteristic wavelengths of the color filters belonging to a color channel differ from one another in each case between the subcells of a supercell.

In other solutions relying on the use of an optical grating in combination with microlens arrays to evaluate spectral information, the resolution of the color image is too low. Moreover, the entire set-up is comparatively complex and requires a high outlay in respect of assembly. Here, too, the solution according to the invention thus affords the advantage that a relatively simple set-up compared with the previously known solution mentioned and relatively simple assembly are made possible.

Advantageous configurations of the invention are described below, which by themselves or in combination with the features of other configurations described herein can optionally be combined together.

In accordance with one advantageous configuration, the characteristic wavelengths can be transmission maximums of the color filters. Relative to the transmission of light, an amplitude of the filter can be the highest at the wavelength of the transmission maximum. Alternatively or additionally, the characteristic wavelength can also be a mean wavelength or a wavelength describing a parameter of a mathematical approximation of a transmission curve.

By way of example, provision can be made for the characteristic wavelengths of at least one color channel, preferably of all the color channels, to be separated from one another in such a way that the associated transmission maxima of the color filters are distinguishable from one another.

In accordance with an embodiment variant as an alternative or supplementary to the solutions mentioned above, provision can be made for at least one supercell to have at least two subcells which have the same characteristic wavelength for at least one color channel and/or for at least one color filter. Preferably, provision can alternatively or supplementarily be made for there to be at least two subcells within a supercell which differ in the characteristic wavelength of at least one color filter.

In accordance with a further advantageous configuration, provision can be made for the supercells each to have at least four subcells. Consequently, a color image of high spatial resolution and to supplement that spectroscopic additional information can be detected with the aid of the sensor array.

In order to obtain a good resolution of the recorded image, the supercells can each have a rectangular or square pattern composed of subcells. In particular, the supercells can have a pattern having the same number of subcells per row ($Z_n$) and subcells per column ($S_n$) or a different number of subcells per row ($Z_{n+1}$; $Z_{n+2}$; ... $Z_{n+x}$; $Z_{n-1}$, $Z_{n-2}$; ... $Z_{n-x}$) and subcells per column ($S_n$). Preferably, this can be a pattern or a combination of two or more patterns selected from 2×2 subcells, 3×3 subcells, 4×4 subcells, 5×5 subcells, 6×6 subcells, 2×3 subcells, 3×2 subcells, 3×4 subcells, 4×3 subcells, 4×5 subcells, 5×4 subcells, 5×6 subcells, 6×5 subcells, 2×4 subcells, 4×2 subcells, 3×5 subcells, 5×3 subcells, 4×6 subcells, 6×4 subcells.

In accordance with a further advantageous configuration, provision can be made for the subcells each to have at least four photocells.

In order to obtain a good resolution of the hyperspectral image, the subcells can each have a rectangular or square pattern composed of photocells. Preferably, the subcells can have a pattern having the same number of photocells per row ($R_n$) and photocells per column ($C_n$) or a different number of photocells per row ($R_{n+1}$; $R_{n+2}$; ... $R_{n+x}$; $R_{n-1}$, $R_{n-2}$; ... $R_{n-x}$) and photocells per column ($C_n$). It can be particularly preferred here if this is a pattern or a combination of two or more patterns selected from 2×2 photocells, 3×3 photocells, 4×4 photocells, 5×5 photocells, 6×6 photocells, 2×3 photocells, 3×2 photocells, 3×4 photocells, 4×3 photocells, 4×5 photocells, 5×4 photocells, 5×6 photocells, 6×5 photocells, 2×4 photocells, 4×2 photocells, 3×5 photocells, 5×3 photocells, 4×6 photocells, 6×4 photocells.

In order to be able to record a color image with sufficient quality, in particular with a good color temperature, in accordance with one advantageous development, provision can be made for the subcells each to have at least three color filters. Here the at least three color filters can be assigned in each case to different color channels. What can thus be achieved is that each subcell in each of the color channels which span the visible spectrum has at least one detecting photocell. In other words, each subcell for each color channel of a set of color channels spanning the visible spectrum has at least one color filter.

Preferably, the color channels of the subcells are distributed among the photocells according to a uniform pattern. The assignment of the color channels to the photocells can also be selected such that a subcell displaced horizontally or vertically by one photocell again represents a subcell in this sense. This enables a color recording with a resolution that is higher than should be expected from the subdivision into subcells.

Alternatively or supplementarily thereto, provision can be made for the subcells to have at least one additional filter, the characteristic wavelength of which lies outside the visible spectrum. In particular, a transmission maximum of the at least one additional filter can be at a wavelength in the UV range and/or IR range.

In accordance with a further advantageous configuration of the sensor array, provision can be made for the characteristic wavelengths of adjacent color filters of different subcells of a supercell which are assigned to an identical color channel to have an equidistant separation or an unequal separation with respect to one another. In particular, provision can be made here for the characteristic wavelengths of all adjacent color filters of a supercell which are assigned to an identical color channel to have an equidistant separation and/or an unequal separation with respect to one another.

In accordance with a further advantageous configuration of the sensor array, provision can be made for a separation of the characteristic wavelengths between two adjacent color filters of one color channel in a supercell to be equal or not equal to a separation of the characteristic wavelengths between two adjacent color filters of another color channel in the supercell. In particular, provision can be made here for a separation of the characteristic wavelengths between all adjacent color filters of one color channel in a supercell to be equal or not equal to a separation of the characteristic wavelengths between all adjacent color filters of another color channel in the supercell.

Alternatively or supplementarily, in accordance with a further configuration, provision can be made for the characteristic wavelengths of the color filters of different color channels of the subcells of a supercell to have an equidistant separation and/or an unequal separation with respect to one another.

In accordance with one advantageous development, provision can be made for the occupation arrangements of the color filters associated with a color channel in the subcells of one supercell to be identical or different. In particular, provision can be made here for the occupation arrangements of the color filters associated with a color channel in the subcells of all the supercells to be identical or different.

Alternatively or supplementarily thereto, in accordance with one development, provision can be made for the occupation arrangements of the subcells within one supercell to be identical or different. In particular, provision can be made here for the occupation arrangements of the subcells within all the supercells to be identical or different.

In order to be able to embody a configuration that saves as much space as possible, in accordance with one advantageous development of the sensor array, provision can be made for the individual filters (color filters and/or the additional filters) of the sensor array to be arranged in a filter plane, in particular in exclusively one filter plane. In comparison with sensor arrays comprising a plurality of filter planes or one filter plane and at least one supplementary filter arranged in the optical beam path, a significantly more compact configuration of a sensor array is thus possible. Preferably, the filter plane of the sensor array can be integrated on the image sensor, that is to say in particular fixedly connected thereto. This has the advantage that it is possible already to define a spatial assignment for example in the course of a lithography method and there is no need for subsequent adjustment of the filters relative to the image sensor.

Consequently, single-stage color filters are usable for the invention. This does not preclude further filters being disposed upstream or downstream for other purposes. In this case, the characteristic wavelengths can be related to these single-stage color filters.

In accordance with one advantageous configuration of the sensor array, provision can be made for a supercell structure and/or a subcell structure of the sensor array to be repeated periodically, in particular in an identical occupation arrangement. A simple evaluation is thus possible since pixel arrangements going beyond a subcell can be treated as averaged values in an evaluation step.

It is particularly expedient if the supercells are constructed identically. The measurement values from the photocells of a supercell are thus comparable with the measurement values from the photocells of an adjacent supercell. It is thus possible to obtain a spatially resolved measurement value distribution with respect to the different characteristic wavelengths.

In order to be able to record as many bands as possible by the sensor array, in order to be able to generate a hyperspectral image of high resolution, a filter width with which at least one color filter and/or at least one additional filter allow(s) a transmission can be from 8 nm to 25 nm, in particular from 10 nm to 20 nm. In particular, all the color filters of one color channel and/or of all the color channels and/or all the additional filters can have the same filter width. Alternatively or supplementarily thereto, provision can be made for the color filters and/or additional filters to be at least in part interference filters. It is thus possible to establish particularly narrow passbands of the individual filters.

In accordance with a further advantageous configuration, provision can be made for the bandwidths of two adjacent color filters of a color channel in a supercell and/or of two adjacent additional filters in a supercell to overlap. In particular, provision can be made here for the bandwidths of all adjacent color filters of a color channel in a supercell and/or of all adjacent additional filters in a supercell to overlap.

Alternatively or supplementarily, in accordance with a further advantageous configuration, provision can be made for a gap to be provided between the bandwidths of two adjacent color filters of a color channel in a supercell and/or between the bandwidths of two adjacent additional filters in a supercell. In particular, provision can be made here for a gap to be provided between the bandwidths of all adjacent color filters of a color channel in a supercell and/or between the bandwidths of all adjacent additional filters in a supercell. It can be particularly advantageous here if an overlap range is narrower than half of a filter width of the color filters and/or of the additional filters. It can be further preferred if the gap is narrower than half of the filter width of the color filters and/or of the additional filters.

In order to achieve an almost corresponding sensitivity, provision can be made for the amplitudes of the color filters of a color channel of a supercell to be equal in magnitude or almost equal in magnitude. In particular, provision can be made here for the amplitudes of the color filters of a color channel of all the supercells to be equal in magnitude or almost equal in magnitude. Provision can also be made for the amplitudes of the color filters to be adapted to a sensitivity function or spectral sensitivity of the sensor, for example in order to achieve a uniform sensitivity. This is particularly expedient if the sensitivity of the sensor is greatly dependent on the wavelength.

In order to be able to record as many closely disposed, in particular successive, wavelengths as possible with a supercell, in accordance with one advantageous development of the sensor array, provision can be made for there to be no corresponding characteristic wavelengths of the color filters belonging to a color channel in the case of the subcells of a supercell.

In accordance with one advantageous development, provision can be made for an individual tuning of the color filters of a color channel in a supercell to be effected by means of an alteration of the characteristic wavelength.

The invention furthermore relates to a method for calculating a color image and a hyperspectral image using a sensor array as described and/or claimed herein. In particular, provision can be made here for spectroscopic measurement values in the characteristic wavelengths of the color filters and/or additional filters assigned to the photocells to be output and/or used as a calculation basis for calculating an image. The method according to the invention thus makes it possible to record a color image of high resolution and spectroscopic measurement values assigned spatially to the color image, in particular to the image scene of the color image, by means of an image sensor, in particular a single image sensor.

It is particularly expedient here if the measurement values are output and/or used in a manner ordered according to the characteristic wavelengths, for example by means of a specific data format for the measurement values. Alternatively or additionally, provision can be made for the measurement values to be output and/or used jointly with the assigned characteristic wavelengths. Consequently, an assignment of the measurement values to the wavelength for which they were obtained is directly available.

The invention furthermore additionally relates to a method for carrying out a white balance for a sensor array for recording a color image. In particular, the method for carrying out a white balance is suitable for a sensor array as described and/or claimed herein. Provision can be made here for a location-dependent white point, in particular a subcell-dependent white point, to be determined and a location-specific white balance, in particular subcell-specific white balance, to be carried out.

In accordance with one advantageous development of the method, provision can be made for the white points of different subcells in a supercell to deviate from one another and/or for the white points of identical subcells, in particular of different supercells, to be identical.

The invention additionally relates to the use of a sensor array as described and/or claimed herein in medical imaging. In particular, the sensor array can be used in an endoscope. As already explained above, the sensor array has the advantage over previously known sensor arrays that it can be configured particularly compactly. Consequently, a space requirement of the sensor array is smaller in comparison with previously known sensor arrays. Particularly in the case of endoscopes used in the medical field, consideration should be given to ensuring that specific sizes are complied with and evolution of heat is minimized. Reducing the space requirement of the sensor array thus makes it possible to provide particularly narrow endoscopes that can be inserted even into difficult to access, in particular narrow, cavities. Furthermore, owing to the use of just one image sensor, it is possible to reduce the evolution of heat by comparison with sensor arrays comprising two or more image sensors.

BRIEF DESCRIPTION OF THE DRAWINGS

The invention will now be described in greater detail on the basis of a number of exemplary embodiments, but is not restricted to these exemplary embodiments. Further exemplary embodiments arise through the combination of the features of individual or a plurality of claims among one another and/or with individual or a plurality of features of the exemplary embodiments.

In the figures.

DETAILED DESCRIPTION

Figure 1:
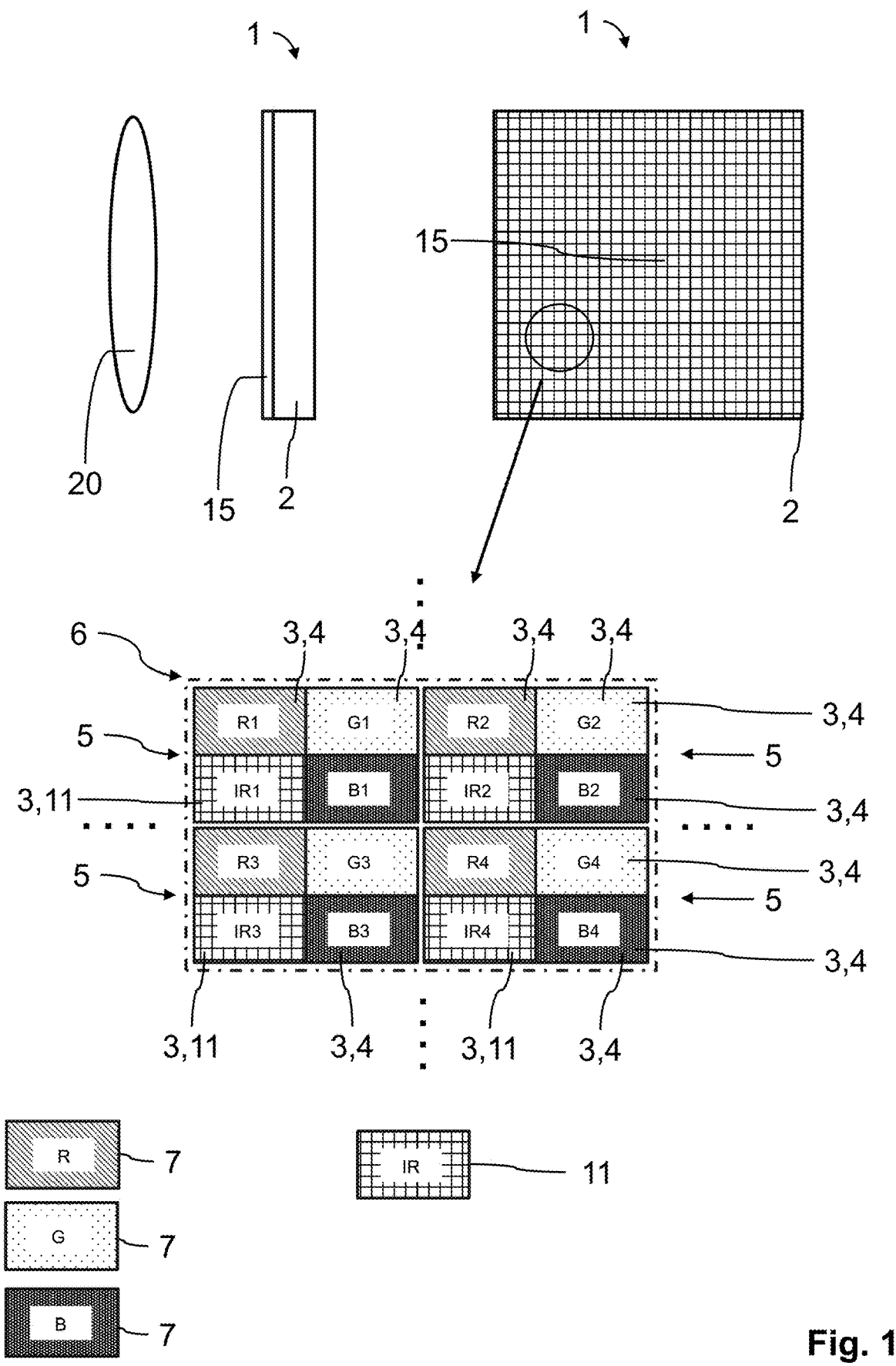
FIG. 1 shows a schematic illustration of one possible configuration of a sensor array according to the invention comprising subcells (1=top left, 2=top right, 3=bottom left, 4=bottom right) each consisting of 2×2 photocells (with the filter properties R1, R2, R3, R4, G1, G2, G3, G4, B1, B2, B3, B4, IR1, IR2, IR3, IR4), wherein the lower half of the figure shows a detailed view of the encircled region of the entire sensor array, having a supercell composed of 2×2 subcells (corresponds to 4×4 photocells), which reveals the filter occupation of the individual photocells, wherein for the three color channels R stands for Red, G stands for Green and B stands for Blue, and wherein the sensor array has one additional filter (IR) in the infrared range, for example, per subcell, and wherein the supercell illustrated in detail at the bottom is followed by further supercells, in particular having the same size and/or having the same pattern of subcells.
Figure 2:
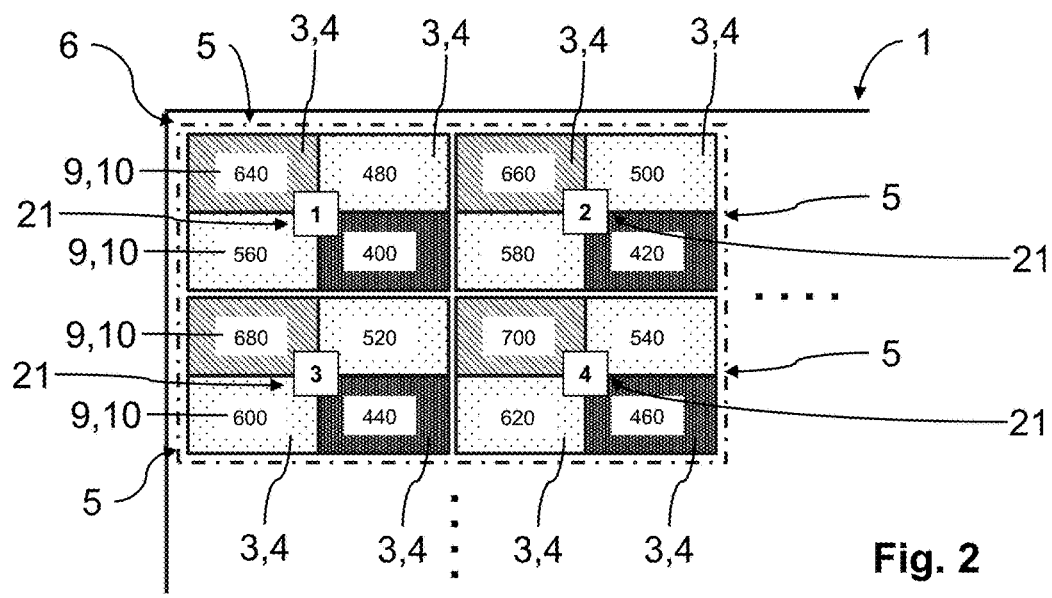
FIG. 2 shows a further schematic detailed view of a supercell of one possible embodiment variant of a sensor array according to the invention comprising four color channels (1×R, 2×G, 1×B), preferably comprising four color filters, which have a characteristic wavelength within the spectrum visible to the human eye and were chosen so as to include the primary colors of the visible range (1×R, 2×G, 1×B), wherein the subcells are constructed from 2×2 photocells and the supercells are constructed from 2×2 subcells (corresponds to 4×4 photocells), wherein the characteristic wavelengths of the individual color filters correspond to the numerical values indicated, wherein, between adjacent color filters of a color channel, the characteristic wavelength is tuned by a difference magnitude of 20 nm in each case, said difference magnitude remaining constant in each case relative to the color filters of a color channel, wherein the supercell shown is followed by further supercells.
Figure 3:
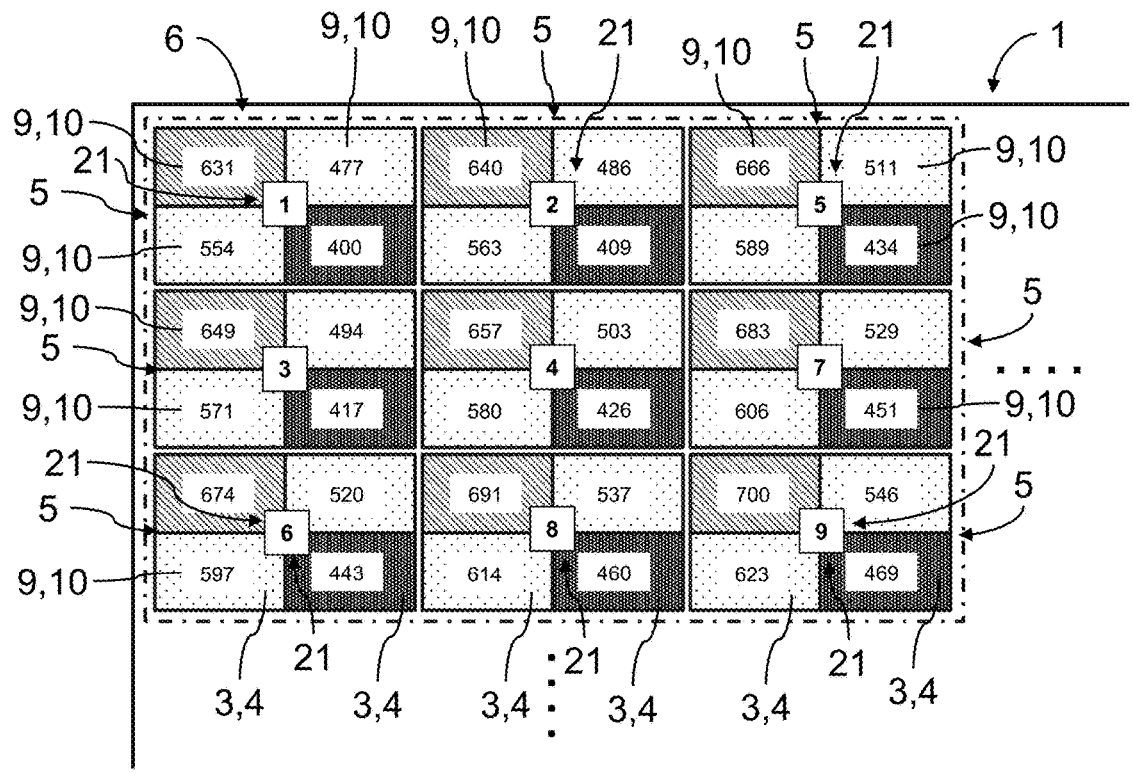
FIG. 3 shows a further schematic detailed view of a supercell of one possible embodiment variant of a sensor array according to the invention comprising four color channels (1×R, 2×G, 1×B), preferably comprising four color filters, which have a characteristic wavelength within the spectrum visible to the human eye and were chosen so as to include the primary colors of the visible range (1×R, 2×G, 1×B), wherein the subcells are constructed from 2×2 photocells and the supercells are constructed from 3×3 subcells (corresponds to 6×6 photocells), wherein the characteristic wavelengths of the individual color filters correspond to the numerical values indicated, wherein, between adjacent color filters of a color channel, the characteristic wavelength is tuned by a respectively varying difference magnitude (separation) wherein the supercell shown is followed by further supercells.

FIGS. 1, 2 and 3 each show a sensor array designated in its entirety as 1.

Sensor arrays 1 are generally semiconductor-based devices that make it possible to record two-dimensional images of an image scene. In this case, sensor arrays 1 are already known which are based on monochromatic image sensors 2 provided with a plurality of color filters 4 in order to allow light of a specific wavelength to impinge on the photocells 3 respectively situated underneath.

The sensor array 1 is configured to be able to record, by means of an image sensor 2, in particular by means of a monochromatic image sensor 2, a color image and in addition thereto a hyperspectral image by means of the acquisition of spectroscopic information. What is crucial here is a correct spatial assignment of the spectroscopic information to the image scene of the color image.

The upper half of FIG. 1 firstly shows a rough schematic set-up of one possible embodiment variant of a sensor array 1. The latter comprises an image sensor 2 equipped with a filter plane 15 having a plurality of individual filters (e.g. color filters 4 and/or additional filters 11), said filter plane being integrated on the image sensor 2, in particular. In this case, the individual filters are fixedly assigned to the photocells 3 of the image sensor 2, such that each individual filter preferably covers only exactly one photocell 3 situated underneath. The photocells 3 detect a brightness value of the light of a characteristic wavelength 9 that is transmitted through the individual filters. The sensor array 1 has the advantage that as a result of only one filter plane there is a particularly small space requirement. Moreover, the orientation of the single-stage individual filters relative to the photocells 3 is easier than in the case of two or more filter planes 15.

The lower half of FIG. 1 shows a schematic illustration of the occupation of the image sensor 2 with individual filters. The photocells 3 equipped with individual filters are grouped in subcells 5 composed of in each case 2×2 photocells 3. In the embodiment variant illustrated, four subcells 5 combine to form a supercell 6, which is constructed in a pattern of 2×2 subcells. However, other patterns of subcells 5 and/or supercells 6 are also possible, as is also described thoroughly further below.

Each photocell 3 is assigned to only one subcell 5. Each subcell 5 in turn is assigned to only one supercell 6.

Each subcell 5 covers a color channel 7,R,G,B,A,C,D, by way of a color filter 4, in particular a partial range (band) of a color channel 7,R,G,B,A,C,D. All the color channels 7,R,G,B,A,C together cover at least the spectral range of the primary colors of the visible range—also referred to hereinafter as visible spectrum 8 (to the human eye)—in particular exactly the visible spectrum 8. The range of from 380 nm to 780 nm can be understood as the visible spectrum 8.

Each individual filter (that is to say each color filter 4 and/or each additional filter 11) has a characteristic wavelength 9. The individual filters of different subcells 5 of a supercell 6 are detuned/tuned with respect to one another. Consequently, the characteristic wavelengths 9 of the individual filters of a supercell which belong to a channel 7,R,G,B,A,C,D (for example to a color channel 7,R,G,B, A,C and/or to a channel D in a range outside the visible spectrum 8) in each case deviate from one another. Adjacent individual filters of a channel 7,R,G,B,A,C,D which have the smallest separations 12, 13, 14, 22 in the characteristic wavelengths 9, with their passbands, can overlap in an overlap range 17 or a gap 18 can be formed therebetween. A gap 18 can be understood to mean, in particular, a range of the respective channel spectrum whose wavelength is not transmitted by any individual filter of the channel.

The characteristic wavelength 9 can relate to a respective transmission maximum of the individual filters.

In the exemplary embodiment, R1, R2, R3, R4, G1, G2, G3, G4, B1, B2, B3, B4, IR1, IR2, IR3, IR4 are different in pairs.

In a further exemplary embodiment of the invention, the characteristic wavelengths differ only in part. By way of example, R1=R2=R3=R4 and/or G1=G2=G3=G4 and/or B1=B2=B3=B3 can hold true, while IR1, IR2, IR3, IR4 are different in pairs. In further exemplary embodiments, other combinations of the correspondence and of the differences are realized.

The supercell 6 from FIG. 1 covers a total of three color channels 7,R,G,B,A,C, wherein R corresponds to the red channel, G corresponds to the green channel and B corresponds to the blue channel. Each subcell 5 furthermore has an additional filter 11, which is assigned to a channel D that covers a range outside the visible spectrum 8 (such as infrared and/or ultraviolet radiation, for example). Each of the four subcells 5 of the supercell 6 has in each case four photocells 3 with a fixedly assigned individual filter (with the filter properties R1, R2, R3, R4, G1, G2, G3, G4, B1, B2, B3, B4, IR1, IR2, IR3, IR4), wherein the nine color filters 4 of the supercell 6 are assigned respectively to one of the color channels 7,R,G,B,A,C, such that respectively three color filters 4 are present per color channel 7,R,G,B,A,C.

The photocells 3 can have a square or rectangular shape. The supercells 6 can likewise have a rectangular or square pattern composed of subcells 5. The subcells 5 in turn can likewise have a rectangular or square pattern comprised of photocells 3.

In this case, the pattern chosen can define the maximum achievable image resolution of the sensor array 1. Some examples of possible patterns are mentioned below, although the invention is not restricted to the patterns mentioned. In principle, it is necessary here to weigh up between the spatial resolution and the number of hyperspectral measurement values.

The supercells 6 can have for example a pattern comprising an identical number of subcells 5 per row $(Z_n)$ and subcells per column $(S_n)$, as is shown in FIGS. 1, 2, 3 and 5. Patterns having a different number of subcells 5 per row $(Z_{n+1}; Z_{n+2}; \ldots Z_{n+x}; Z_{n-1}, Z_{n-2}; \ldots Z_{n-x})$ and subcells 5 per column $(S_n)$ are not illustrated, but are likewise covered by the invention.

Preferred patterns of supercells 6 can for example be selected from 2×2 subcells, 3×3 subcells, 4×4 subcells, 5×5 subcells, 6×6 subcells, 2×3 subcells, 3×2 subcells, 3×4 subcells, 4×3 subcells, 4×5 subcells, 5×4 subcells, 5×6 subcells, 6×5 subcells, 2×4 subcells, 4×2 subcells, 3×5 subcells, 5×3 subcells, 4×6 subcells, 6×4 subcells.

The subcells 5 can have a pattern comprising the same number of photocells 3 per row $(R_n)$ and photocells 3 per column $(C_n)$, as is shown in FIGS. 1, 2, 3 and 5. Alternatively or supplementarily, the subcells 5 can have patterns comprising a different number of photocells 3 per row $(R_{n+1}; R_{n+2}; \ldots R_{n+x}; R_{n-1}, R_{n-2}; \ldots R_{n-x})$ and photocells 3 per column $(C_n)$. Preferred patterns of subcells 5 can be for example patterns selected from 2×2 photocells, 3×3 photocells, 4×4 photocells, 5×5 photocells, 6×6 photocells, 2×3 photocells, 3×2 photocells, 3×4 photocells, 4×3 photocells, 4×5 photocells, 5×4 photocells, 5×6 photocells, 6×5 photocells, 2×4 photocells, 4×2 photocells, 3×5 photocells, 5×3 photocells, 4×6 photocells, 6×4 photocells.

The detuning of the individual filters (color filters 4 and/or additional filters 11) which are assigned to a channel (color channel 7,R,G,B,A,C and/or additional channel D outside the visible range) can be achieved by virtue of the fact that the characteristic wavelengths 9 of the individual filters, in particular adjacent individual filters, associated with a channel are offset in each case by an equidistant separation 12, 13, 14, 22 and/or an unequal separation 12, 13, 14, 22 with respect to one another. Each individual filter of a channel thus covers a different partial range of the entire channel spectrum. Preferably, all the individual filters of a channel 7,R,G,B,A,C,D (with their passbands) together cover the entire channel spectrum, that is to say in particular all wavelengths of the entire channel spectrum.

FIGS. 2 and 3 show different embodiment variants of a sensor array 1, here the illustration showing in each case a supercell 6 composed of subcells respectively having 2×2 photocells 3, which is followed by further, in particular structurally identical, supercells 6. In the case of the supercells 6 illustrated, in contrast to the supercell 6 from FIG. 1, no channel 7,R,G,B,A,C outside the visible range 8 is provided. Instead, the supercells each have a further green color channel G (wavelengths of 477 nm to 623 nm), such that each subcell 5 of the supercells 6 has two green color filters 4, which differ in their characteristic wavelength 9.

The supercell 6 from FIG. 2 has 2×2 subcells 5 (Nos 1-4), that is to say two subcells 5 per row and two subcells 5 per column. As is evident on the basis of the characteristic wavelength 9 indicated in the center of each photocell 3, the individual color filters 4 of a color channel 7, R,G,B,A,C respectively have an offset by a uniform difference magnitude (separation 12, 13, 14). The separations 12, 13, 14 are each exactly 20 nm in this case. However, it is also conceivable for the separations 12, 13, 14 to differ among the at least three (here four) color channels 7,R,G,B,A,C. Alternatively or supplementarily, it is possible for the separations 12, 13, 14, 22 between the individual filters (such as e.g. the color filters 4 and/or the additional filter 11) within a channel 7,R,G,B,A,C,D in each case to remain uniform or at least partly to deviate from one another.

One example of different separations 12, 13, 14, 22 between the characteristic wavelengths 9 of the individual filters is shown in FIG. 3. FIG. 3 shows a supercell 6 composed of 3×3 subcells 5 (Nos 1-9). The separations 12, 13, 14, 22 between the individual filters (in this case color filters 4) of a channel 7, R,G,B,A,C,D (in this case a color channel 7, R,G,B,A,C) are chosen to be nonuniform. In this regard, the separation 12, 13, 14, 22 between adjacent individual filters of a channel 7,R,G,B,A,C,D here is alternately 9 nm and 8 nm.

Generally it can therefore be stated that the separations 12, 13, 14, 22 can be chosen freely, depending on how close together the detected spectroscopic measurement values are intended to be. In this case, it has proved to be advantageous if the separations 12, 13, 14, 22 of the characteristic wavelengths 9 between adjacent individual filters (color filters 4 and/or additional filters 11) are from 5 nm to 40 nm, in particular from 5 nm to 30 nm, in particular from 5 nm to 25 nm, in particular from 7 nm to 20 nm, in particular from 8 nm to 15 nm.

FIGS. 4 to 7 show further examples of possible configurations of a sensor array 1 according to the invention.

Figure 4:
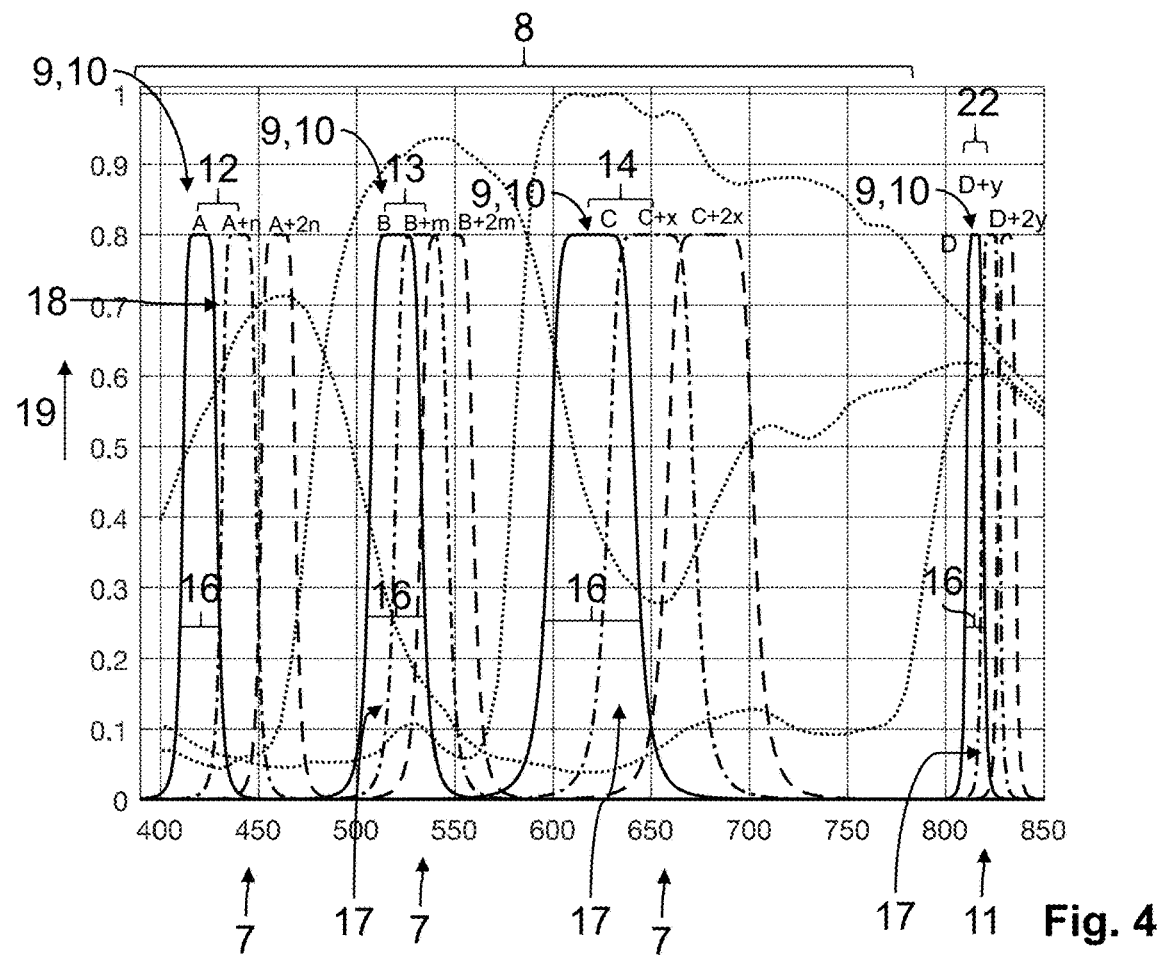
FIG. 4 shows a spectrum covered by the three subcells of a supercell (composed of 3×3 subcells) shown in FIG. 5, wherein the channels A, B and C represent color channels in the range visible to human beings (color range) and the channel D represents a channel outside the visible range (in this case in the infrared range), wherein n, m, x and y indicate the difference magnitudes (separations) between the characteristic wavelengths of the individual filters of a channel between the adjacent subcells, wherein the color filters (A, A+n, A+2n) of the blue color channel have no overlapping bandwidths, wherein the color filters (B, B+m, B+2m) of the green color channel have overlapping bandwidths, and wherein the color filters (C, C+x, C+2x) of the red color channel have even more widely overlapping bandwidths, wherein the filter widths of the additional filters (D, D+y, D+2y) are configured to be significantly narrower than the filter widths of the color filters and therefore only overlap very narrowly.
Figure 5:
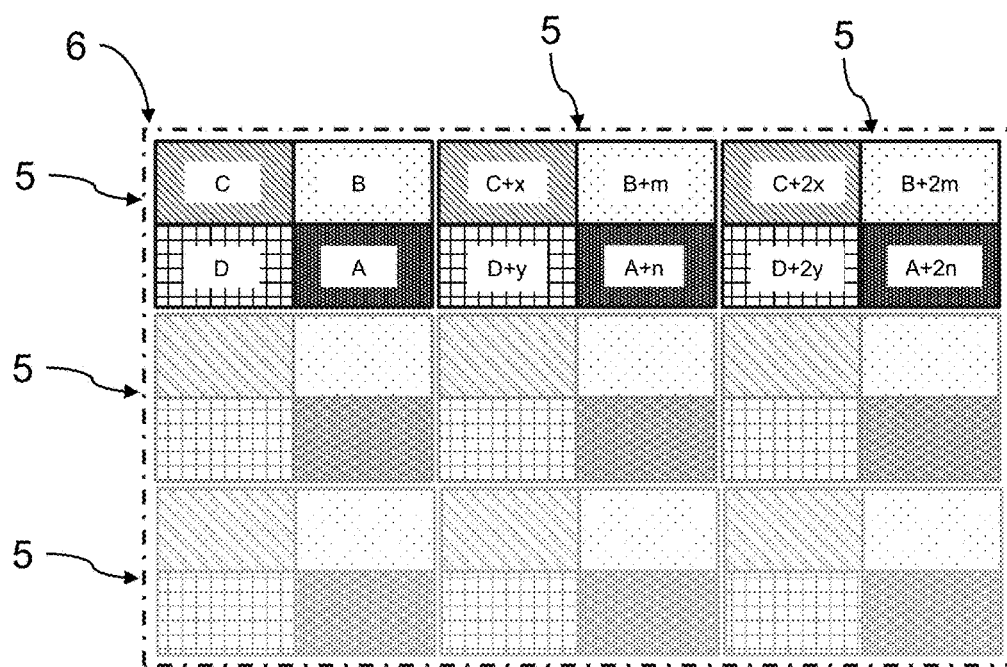
FIG. 5 shows the schematic detailed view of the occupation of the three subcells of the supercell whose filter properties are shown in FIG. 4.

The spectrum shown in FIG. 4 is to be assigned to the occupation shown in FIG. 5. A here stands for the blue color channel, B stands for the green color channel, C stands for the red color channel and D stands for the additional channel outside the visible range 8 (here in the IR range). The separations 12, 13, 14, 22 between the individual filters of a channel (color channel 7,R,G,B,A,C and/or additional channel D) are indicated by the letters n, m, x and y.

As is evident with reference to FIG. 4, the filter widths 16 and the characteristic wavelengths 9 (A, A+n, A+2n) of the color filters 4 of the blue color channel A are chosen such that there is no overlap range 17 between adjacent color filters 4 of the blue color channel A. Rather, mention may be made of gaps 18 between the passbands covered by the individual color filters 4 of the blue color channel A.

In contrast thereto, in the case of the individual filters of the other channels (green-B, red-C, IR-D), an overlap range 17 between the passbands of adjacent individual filters of a channel 7,R,G,B,A,C,D can be discerned.

However, the invention amounts to more than the previous configuration. The characteristic wavelengths 9 and/or the filter widths 16 of the individual filters of the different channels 7,R,G,B,A,C,D can be selected in line with requirements, such that a decision as to whether or not an overlap of the passbands is expedient can be taken in an application-specific manner.

Moreover, a width of an overlap range 17 between two individual filters can be set in particular depending on a chosen characteristic wavelength 9 and a filter width 16.

FIG. 4 furthermore shows an exemplary selection of individual filters having different filter widths 16. In this regard, filter width 16 can relate to a passband from a lower wavelength to an upper wavelength, wherein the individual filter allows light at the specific wavelengths to pass. By contrast, radiation having a wavelength outside the filter band 16 cannot pass or can pass only with very great attenuation.

The filter widths 16 of the color filters 4 and of the additional filters 11 here are respectively chosen to be different, such that only the individual filters of a channel each have identical filter widths 16, but the filter widths 16 of the individual filters of different channels are different.

Figure 6:
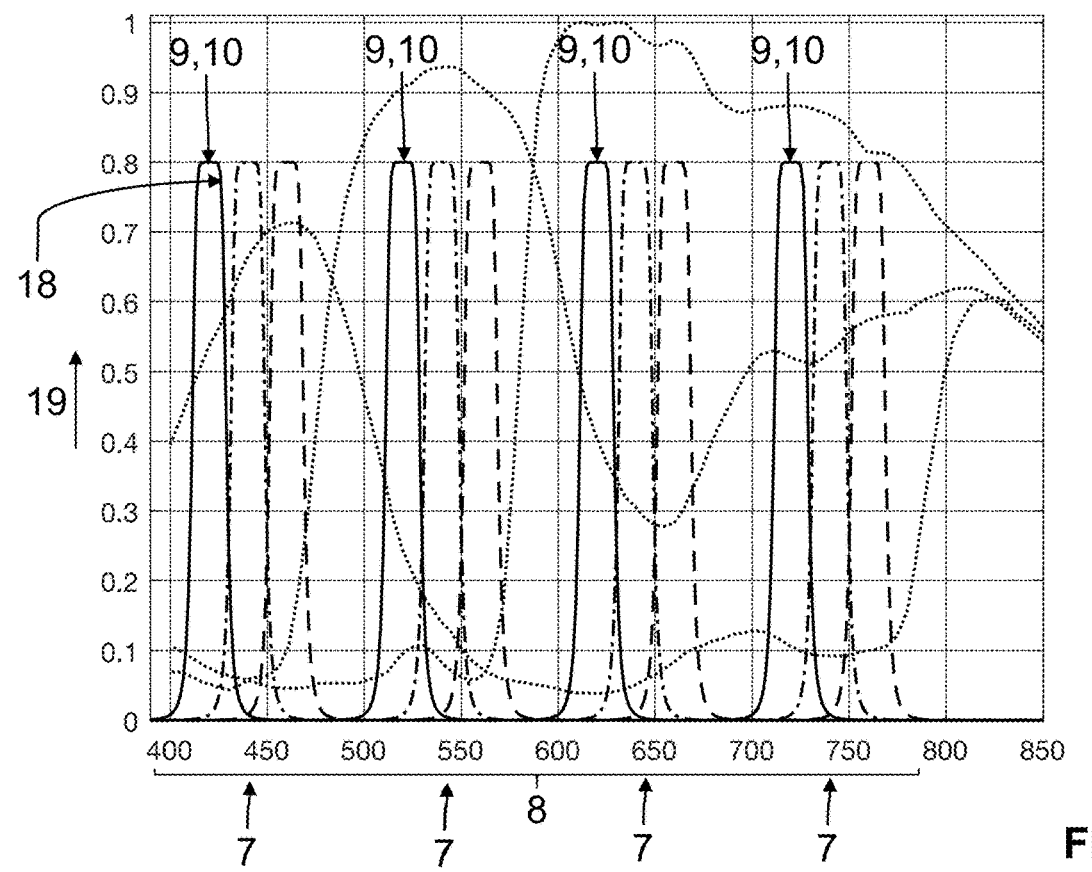
FIG. 6 shows alternative filter properties of the subcells shown in FIG. 5, wherein here a respective gap is provided between each of the individual filters of a channel, wherein the IR channel was exchanged for a further green color channel, wherein the filter widths (bandwidths; passbands) of the individual color filters are identical, and wherein the difference magnitudes (separations) between the characteristic wavelengths of two adjacent individual filters are in each case equal in magnitude.
Figure 7:
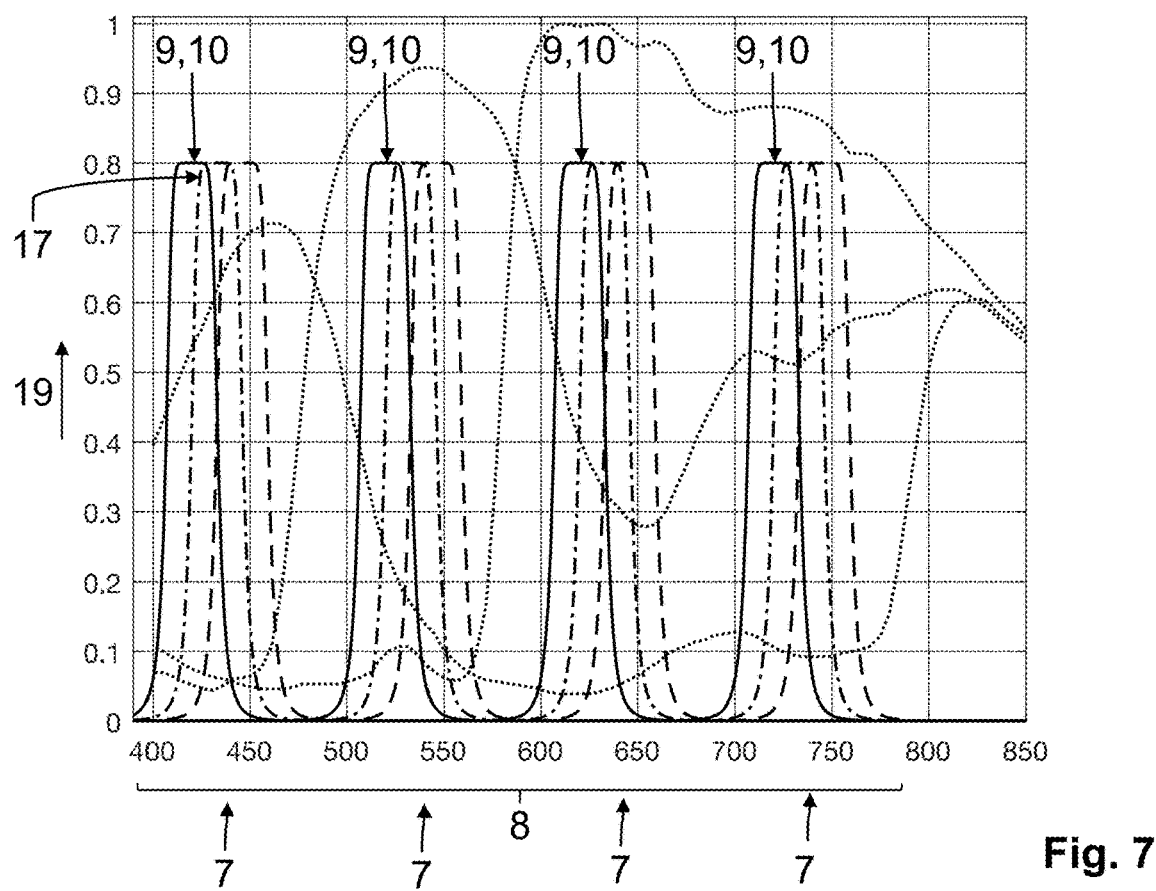
FIG. 7 shows further alternative filter properties of the subcells shown in FIG. 5, wherein here, in contrast to the filter properties from FIG. 6, a respective overlap of the passbands is provided between each of the individual filters of a channel, wherein here, too, the IR channel was exchanged for a further green color channel, wherein the filter widths (bandwidths; passbands) of the individual color filters are identical, and wherein the difference magnitudes (separations) between the characteristic wavelengths of two adjacent individual filters are in each case equal in magnitude.

FIGS. 6 and 7 illustrate two further examples of possible filter properties, wherein in each case identical separations 12, 13, 14 between the passbands of adjacent color filters 4 of a color channel 7,R,G,B,A,C were chosen. The embodiment variants in FIGS. 6 and 7 differ here in the choice of the filter properties of the color filters 4. In this regard, the filter widths 16 in the case of the color filters 4 of the configuration from FIG. 6 are narrower than in the case of the color filters 4 from FIG. 7. Moreover, wider overlap ranges 17 between color filters 4 of a color channel 7,R,G,B,A,C arise in the case of the configuration from FIG. 7.

The filter widths 16 of the individual filters can allow for example a transmission in a passband between a lower wavelength and an upper wavelength, wherein the passband has a width of 8 nm to 25 nm, in particular of 10 nm to 20 nm.

A supercell structure and/or a subcell structure of the sensor array 1 can be repeated periodically, as indicated in FIGS. 1, 2 and 3, in particular in an identical occupation arrangement 21.

The individual filters (color filters 4 and/or additional filters 11) can preferably be configured as interference filters. This has the advantage that a characteristic wavelength 9 is settable particularly accurately and/or in a narrowly delimited way and/or with a lower transmission in the stopband and with a high edge steepness.

As is readily evident with reference to FIGS. 4, 6 and 7, it is particularly advantageous if the amplitudes 19 of the individual filters (color filters 4 and/or additional filters 11) are equal in magnitude or almost equal in magnitude. Alternatively or supplementarily thereto, the amplitudes of the individual filters can be set such that the sensitivities of the individual color channels 7,R,G,B,A,C arising as a result of the combination of the sensitivity of the underlying photocells 3 with the transmission properties of the overlaying color filters 4 are equal in magnitude or almost equal in magnitude. Alternatively or additionally, the amplitudes of the individual filters can be adapted to the spectral sensitivity of the sensor, for example in order to achieve a uniform sensitivity. This can be implemented particularly well in particular by a use of interference filters. Consequently, color images and/or hyperspectral images have a particularly high quality since it is possible to achieve an identical or almost identical intensity during the recording of the light by means of different photocells 3.

As is evident with reference to FIGS. 2 and 3, no corresponding characteristic wavelengths 9 of the color filters 4 belonging to a color channel 7,R,G,B,A,C are provided in the case of the subcells 5 of a supercell 6. A sensor array 1 which can detect a complete spectrum of a color channel 7,R,G,B,A,C by means of a supercell 6 can thus be provided in a relatively confined space.

The above sensor array 1 is thus particularly suitable for replacing existing devices for recording a color image and additional hyperspectral measurement values. The sensor array 1 can be manufactured relatively cost-effectively. Moreover, it is particularly suitable for use in medical imaging, such as in endoscopy, in particular.

By virtue of the use of only one image sensor 2, less waste heat is produced and a more compact design and a lower weight are achieved in comparison with other technical solutions. All these advantages ultimately benefit a user of an image recording device, such as an endoscope, in particular.

Due to its special pattern formation, the sensor array 1 has the special feature that a specific method for carrying out a white balance is provided for recording a color image with optimally represented color temperatures. This involves firstly determining a white point that is location-dependent relative to a coordinate of the sensor array. In this case, the white point can relate to a subcell-dependent white point. After the specific location-dependent white point has been determined, it can be used to carry out a location-specific white balance.

In this case, the white points of different subcells 5 in a supercell 6 can deviate from one another. By contrast, the white points of identical subcells 5, in particular of different supercells 6, can be identical.

The invention thus relates, in particular, to a sensor array 1 for recording a color image in the visible spectrum 8 and hyperspectral information that is spatially linked with the color image, wherein the sensor array 1 comprises an image sensor 2 composed of a plurality of photocells 3, wherein respectively a color filter 4 is fixedly assigned to at least one portion of the photocells 3, wherein each photocell 3 is assigned to a subcell 5 and each subcell 5 is assigned to a supercell 6, wherein each subcell 5 has at least one individual filter of a channel, wherein all the channels together cover at least the primary colors of the visible spectrum 8, wherein the characteristic wavelengths 9 of the individual filters belonging to a channel in each case differ from one another between the subcells 5 of a supercell 6.

LIST OF REFERENCE SIGNS

1 Sensor array
2 Image sensor
3 Photocell
4 Color filter
5 Subcell
6 Supercell
7 Color channel (R,G,B,A,C)
8 Visible spectrum
9 Characteristic wavelength
10 Transmission maximum
11 Additional filter
12 Separation between adjacent color filters of the blue color channel
13 Separation between adjacent color filters of the green color channel
14 Separation between adjacent color filters of the red color channel
15 Filter plane
16 Filter width
17 Overlap range
18 Gap
19 Amplitude
20 Objective lens
21 Occupation arrangement
22 Separation between adjacent additional filters of the additional channel outside the visible range
D Additional channel

The invention claimed is:

1. A sensor array (1) for recording a color image in a visible spectrum (8) and a hyperspectral image, the sensor array comprising:
an image sensor (2) having a plurality of photocells (3), the photocells (3) are assigned at least in part respectively a color filter (4), the photocells (3) are grouped in subcells (5) and the subcells (5) are grouped in supercells (6), wherein there are a plurality of the color channels (7,R,G,B,A,C), which together cover the entire visible spectrum (8) and wherein each said subcell (5) has at least one of the color filters (4) for each color channel in the plurality of color channels (7,R,G,B,A,C), and characteristic wavelengths (9) of the color filters (4) belonging to at least one said color channel (7,R,G,B,A,C), in each case at least partly differ from one another between the subcells (5) of a supercell (6).

2. The sensor array (1) as claimed in claim 1, wherein the characteristic wavelengths (9) are at least one of transmission maximums (10) of the color filters (4) or mean wavelengths (9), and at least one supercell (6) has at least two subcells (5) which have the same characteristic wavelength (9) for at least one of the color channels (7,R,G,B,A,C) or for at least one of the color filters (4) or for at least one of the color channels and at least one of the color filters, and at least two of the subcells (5) within a supercell (6) differ in the characteristic wavelength (9) of at least one color filter (4).

3. The sensor array (1) as claimed in claim 1, wherein the supercells (6) each have at least four subcells (5).

4. The sensor array (1) as claimed in claim 3, wherein the supercells (6) each have a rectangular or square pattern of the subcells (5), the pattern having a same number of subcells (5) per row (Z.sub.n) and the subcells per column (S.sub.n) or a different number of the subcells (5) per row (Z.sub.n+1; Z.sub.n+2; . . . Z.sub.n+x; Z.sub.n−1, Z.sub.n−2; . . . Z.sub.n−x) and the subcells (5) per column (S.sub.n).

5. The sensor array (1) as claimed in claim 1, wherein the subcells (5) each include at least four of the photocells (3).

6. The sensor array (1) as claimed in claim 5, wherein the subcells (5) each have a rectangular or square pattern formed from the photocells (3), the pattern having a same number of the photocells (3) per row (R.sub.n) and the photocells (3) per column (C.sub.n) or a different number of the photocells (3) per row (R.sub.n+1; R.sub.n+2; . . . R.sub.n+x; R.sub.n−1, R.sub.n−2; . . . R.sub.n−x) and the photocells (3) per column (C.sub.n).

7. The sensor array (1) as claimed in claim 1, wherein the subcells (5) each have at least three of the color filters (4) of different ones of the color channels (7,R,G,B,A,C), or the subcells (5) have at least one additional filter (11) that has a characteristic wavelength (9) that lies outside the visible range (8), or the subcells (5) each have at least three of the color filters (4) of different ones of the color channels (7,R,G,B,A,C) and at least one additional filter (11) with a characteristic wavelength (9) that lies outside the visible range (8).

8. The sensor array (1) as claimed claim 1, wherein the characteristic wavelengths (9) of adjacent ones of the color filters (4) of different ones of the subcells (5) of one said supercell (6) which are assigned to an identical one of the color channels (7,R,G,B,A,C) have an equidistant separation (12, 13, 14) with respect to one another, or the characteristic wavelengths (9) of adjacent ones of additional filters (11) that have a characteristic wavelength (9) that lies outside the visible range (8), of different ones of the subcells (5) of one said supercell (6) have an equidistant separation (22) with respect to one another, or the characteristic wavelengths (9) of adjacent ones of the color filters (4) of different ones of the subcells (5) of one said supercell (6) which are assigned to an identical one of the color channels (7,R,G,B,A,C) have an equidistant separation (12, 13, 14) with respect to one another and the characteristic wavelengths (9) of adjacent ones of the additional filters (11) of different ones of the subcells (5) of one said supercell (6) have an equidistant separation (22) with respect to one another.

9. The sensor array (1) as claimed in claim 1, wherein a separation (12, 13, 14) of the characteristic wavelengths (9) between two adjacent ones of the color filters (4) of one said color channel (7,R,G,B,A,C,D) in one said supercell (6) is equal to a separation (12, 13, 14) of the characteristic wavelengths (9) between two adjacent ones of the color filters (4) of another of said color channels (7,R,G,B,A,C) in the supercell (6), or the characteristic wavelengths (9) of the color filters (4) of different ones of the color channels (7,R,G,B,A,C) of the subcells (5) of one said supercell (6) have an equidistant separation with respect to one another, or the characteristic wavelengths (9) between two adjacent ones of the color filters (4) of one said color channel (7,R,G,B,A,C,D) in one said supercell (6) is equal to a separation (12, 13, 14) of the characteristic wavelengths (9) between two adjacent ones of the color filters (4) of another of said color channels (7,R,G,B,A,C) in the supercell (6) and the characteristic wavelengths (9) of the color filters (4) of different ones of the color channels (7,R,G,B,A,C) of the subcells (5) of one said supercell (6) have an equidistant separation with respect to one another.

10. The sensor array (1) as claimed in claim 1, wherein an occupation arrangement of the color filters (4) associated with one said color channel (7,R,G,B,A,C) in the subcells (5) of one said supercell (6) are identical, or an occupation arrangement (21) of the subcells (5) within one said supercell (6) are identical, or the occupation arrangements of the color filters (4) associated with one said color channel (7,R,G,B,A,C) in the subcells (5) of one said supercell (6) are identical and the occupation arrangements (21) of the subcells (5) within one said supercell (6) are identical.

11. The sensor array (1) as claimed in claim 1, wherein at least one of the color filters (4) or additional filters (11), which have a characteristic wavelength (9) that lies outside the visible range (8), of the sensor array (1) are arranged in a filter plane (15), or are embodied as single-stage color filters (4), or are arranged in the filter plane and embodied as single-stage color filters (4).

12. The sensor array (1) as claimed in claim 1, wherein at least one of a supercell structure or a subcell structure of the sensor array (1) is repeated periodically, or the supercells (6) are constructed identically, or at least one of the supercell structure or the subcell structure of the sensor array (1) is repeated periodically and the supercells (6) are constructed identically.

13. The sensor array (1) as claimed in claim 1, wherein a filter width (16) with which at least one of said color filters (4) or at least one additional filter (11) which has a characteristic wavelength (9) that lies outside the visible range (8), allows a transmission is from 8 nm to 25 nm, or at least one of the color filters (4) or the additional filters (11) are at least in part interference filters, or the filter width (16) with which at least one of said color filters (4) or at least one additional filter (11) which has a characteristic wavelength (9) that lies outside the visible range (8), allows a transmission is from 8 nm to 25 nm and at least one of the color filters (4) or the additional filters (11) are at least in part interference filters.

14. The sensor array (1) as claimed in claim 1, wherein bandwidths of two adjacent ones of the color filters (4) of one said color channel (7,R,G,B,A,C) in one said supercell (6) or of two adjacent additional filters (11), which have a characteristic wavelength (9) that lies outside the visible range (8), or both, in one said supercell (6) overlap, or a gap (18) is provided between the bandwidths of two adjacent ones of the color filters (4) of one said color channel (7,R,G,B,A,C) in one said supercell (6) or of two adjacent ones of the additional filters (11) in one said supercell (6), or both.

15. The sensor array (1) as claimed in claim 1, wherein amplitudes (19) of the color filters (4) of one said color channel (7,R,G,B,A,C) of one said supercell (6) are equal in magnitude or almost equal in magnitude.

16. The sensor array (1) as claimed in claim 1, wherein there are no corresponding characteristic wavelengths (9) of the color filters (4) belonging to one said color channel (7,R,G,B,A,C) in the case of the subcells (5) of one said supercell (6).

17. The sensor array (1) as claimed in claim 1, wherein an individual tuning of the color filters (4) of one said color channel (7,R,G,B,A,C) in one said supercell (6) is adapted to be effected by an alteration of the characteristic wavelength (9).

18. A method for calculating a color image and a hyperspectral image using the sensor array (1) as claimed in claim 1, comprising: outputting spectroscopic measurement values in the characteristic wavelengths (9) of at least one of the color filters (4) or additional filters (11), which have a characteristic wavelength (9) that lies outside the visible range (8), assigned to the photocells (3), and using the spectroscopic measurement values as a calculation basis for calculating an image that is at least one of ordered according to the characteristic wavelengths (9) or with the assigned characteristic wavelengths (9).

19. A method for carrying out a white balance for a sensor array (1) for recording a color image using the sensor array (1) as claimed in claim 1, the method comprising: determining a location-dependent white point, and carrying out a location-specific white balance.

20. The method as claimed in claim 19, wherein the white points of different ones of the subcells (5) in one said supercell (6) deviate from one another or the white points of identical subcells (5) are identical, or both.

21. An endoscope comprising the sensor array (1) as claimed in claim 1.

\* \* \* \* \*